US012694966B2

(12) United States Patent
Hakala et al.

(10) Patent No.: US 12,694,966 B2
(45) Date of Patent: Jul. 28, 2026

(54) MACHINE LEARNING MODELING TO PREDICT HEURISTIC PARAMETERS FOR RADIATION THERAPY TREATMENT PLANNING

(71) Applicant: Siemens Healthineers International AG, Steinhausen (CH)

(72) Inventors: Mikko Hakala, Rajamaki (FI); Elena Czeizler, Helsinki (FI); Shahab Basiri, Siuntio (FI); Esa Kuusela, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 1315 days.

(21) Appl. No.: 17/480,056

(22) Filed: Sep. 20, 2021

(65) Prior Publication Data

US 2023/0087944 A1 Mar. 23, 2023

(51) Int. Cl.

| | |
|---|---|
| *G16H 20/40* | (2018.01) |
| *A61N 5/10* | (2006.01) |
| *G06N 3/08* | (2023.01) |
| *G06N 20/00* | (2019.01) |
| *G16H 30/20* | (2018.01) |
| *G16H 50/30* | (2018.01) |

(52) U.S. Cl.
CPC .......... *G16H 20/40* (2018.01); *A61N 5/1031* (2013.01); *A61N 5/1039* (2013.01); *G06N 3/08* (2013.01); *G06N 20/00* (2019.01); *G16H 30/20* (2018.01); *G16H 50/30* (2018.01)

(58) Field of Classification Search
CPC ........ G16H 20/40; G16H 30/20; G16H 50/30; G16H 50/20; G16H 40/20; A61N 5/1031; A61N 5/1039; A61N 5/103; G06N 3/08; G06N 20/00
See application file for complete search history.

(56) References Cited

U.S. PATENT DOCUMENTS

| | | | | |
|---|---|---|---|---|
| 2013/0197878 A1* | 8/2013 | Fiege | ..................... | G06F 30/20 |
| | | | | 703/2 |
| 2014/0164059 A1* | 6/2014 | Dove | ....................... | G06N 5/01 |
| | | | | 705/7.31 |

(Continued)

OTHER PUBLICATIONS

Wei et al. ("Learned Conjugate Gradient Descent Network for Massive MIMO Detection", IEEE Transactions on Signal Processing, vol. 68, 2020, pp. 6336-6349) (Year: 2020).*

(Continued)

*Primary Examiner* — Imad Kassim
(74) *Attorney, Agent, or Firm* — Foley & Lardner LLP

(57) ABSTRACT

Methods and systems for configuring a plan optimizer model for radiotherapy treatment is presented herein in which a processor iteratively trains a machine learning model configured to predict a heuristic parameter, wherein with each iteration, an agent of the machine learning model identifies a test heuristic parameter; transmits the test heuristic parameter to the plan optimizer model configured to receive one or more radiotherapy treatment attributes and predict a treatment plan; and identifies a reward for the test heuristic parameter based on execution performance value of the plan optimizer model, wherein the processor iteratively trains a policy of the machine learning model until the policy satisfies an accuracy threshold based on maximizing the reward.

20 Claims, 8 Drawing Sheets

(56) References Cited

U.S. PATENT DOCUMENTS

| | | | | |
|---|---|---|---|---|
| 2014/0253324 A1* | 9/2014 | Tamez | ............... | G08B 21/0461 |
| | | | | 340/539.12 |
| 2020/0303068 A1* | 9/2020 | Osogami | .............. | G06N 3/0464 |
| 2020/0353286 A1* | 11/2020 | Wu | ........................ | A61N 5/1031 |
| 2021/0027878 A1* | 1/2021 | He | ......................... | G16H 50/70 |
| 2021/0379404 A1* | 12/2021 | Basiri | .................. | A61N 5/1038 |
| 2022/0088410 A1* | 3/2022 | Hibbard | ............... | A61N 5/1038 |

OTHER PUBLICATIONS

International Preliminary Report on Patentability for PCT App. PCT/US2022/043019 dated Mar. 26, 2024 (12 pages).

Aleman D M et al: "Computational enhancements to fluence map optimization for total marrow irradiation using IMRT", Computers and Operations Research, vol. 40, No. 9, Sep. 1, 2013 (Sep. 1, 2013), pp. 2167-2177, XP055533251, GB ISSN: 0305-0548, DOI: 10.1016/j.cor.2011.05.028 abstract p. 2169 col. 2 par.4; p. 2173 col. 1 par.2.

Hakala M et al: "Reinforcement Learning to Speed Up Conjugate Gradient Optimization in IMRT. Annual Meeting of the American Association of Physicists in Medicine, AAPM 2022." Medical Physics, vol. 49, No. 6, Jun. 9, 2022 (Jun. 9, 2022), pp. e904-e904, XP093007132, Retrieved from the Internet: URL:https://aapm.onlinelibrary.wiley.com/doi/epdf/10.1002/mp.15769> [retrieved on Dec. 12, 2022] the whole document.

International Search Report and Written Opinion on PCT/US2022/043019 dated Dec. 21, 2022 (20 pages).

Shen C et al: "A hierarchical deep reinforcement learning framework for intelligent automatic treatment planning of prostate cancer intensity modulated radiation therapy", Physics in Medicine and Biology, Institute of Physics Publishing, Bristol GB, vol. 66, No. 13, Jun. 23, 2021 (Jun. 23, 2021), p. 134002, XP020367586, ISSN: 0031-9155, DOI: 10.1088/1361-6560/AC09A2 [retrieved on Jun. 23, 2021] abstract p. 3 par.1; Algorithm 1; sections 2.5.1, 2.5.3 and 3.1; figures 1-3.

Tortora M et al: "Deep Reinforcement Learning for Fractionated Radiotherapy in Non-Small Cell Lung Carcinoma", Artificial Intelligence in Medicine, Elsevier, NL, vol. 119, Aug. 15, 2021 (Aug. 15, 2021), XP086778131, ISSN: 0933-3657, DOI: 10.1016/J.ARTMED.2021.102137 [retrieved on Aug. 15, 2021] abstract section "3. Background"; figures 1-2.

Yongjie Li et al: "Ant Colony System for the Beam Angle Optimization Problem in Radiotherapy planning: a Preliminary Study", Evolutionary Computation, 2005. The 2005 IEEE Congress on Edinburgh, Scotland, UK Sep. 2-5, 2005, Piscataway, NJ, USA, IEEE, vol. 2, Sep. 2, 2005 (Sep. 2, 2005), pp. 1532-1538, XP010861890, DOI: 10.1109/CEC.2005.1554871, ISBN: 978-0-7803-9363-9 abstract, p. 1534 col. 2 par.1-p. 1536 col. 1 par.1; figures 1-2.

Zhang J. et al: "An Interpretable Planning Bot for Pancreas Stereotactic Body Radiation Therapy", International Journal of Radiation: Oncology Biology Physics., vol. 109, No. 4, Oct. 25, 2020 (Oct. 25, 2020), pp. 1076-1085, XP093007945, USA ISSN: 0360-3016, DOI: 10.1016/j.ijrobp.2020.10.019 Retrieved from the Internet: URL:https://www.sciencedirect.com/science/article/pii/S0360301620344072/pdfft?md5=fe23c2fdb696b6b12f0286c78387b83e&pid=1-s2.0-S0360301620344072-main.pdf> [retrieved on Dec. 13, 2022] the whole document.

* cited by examiner

200

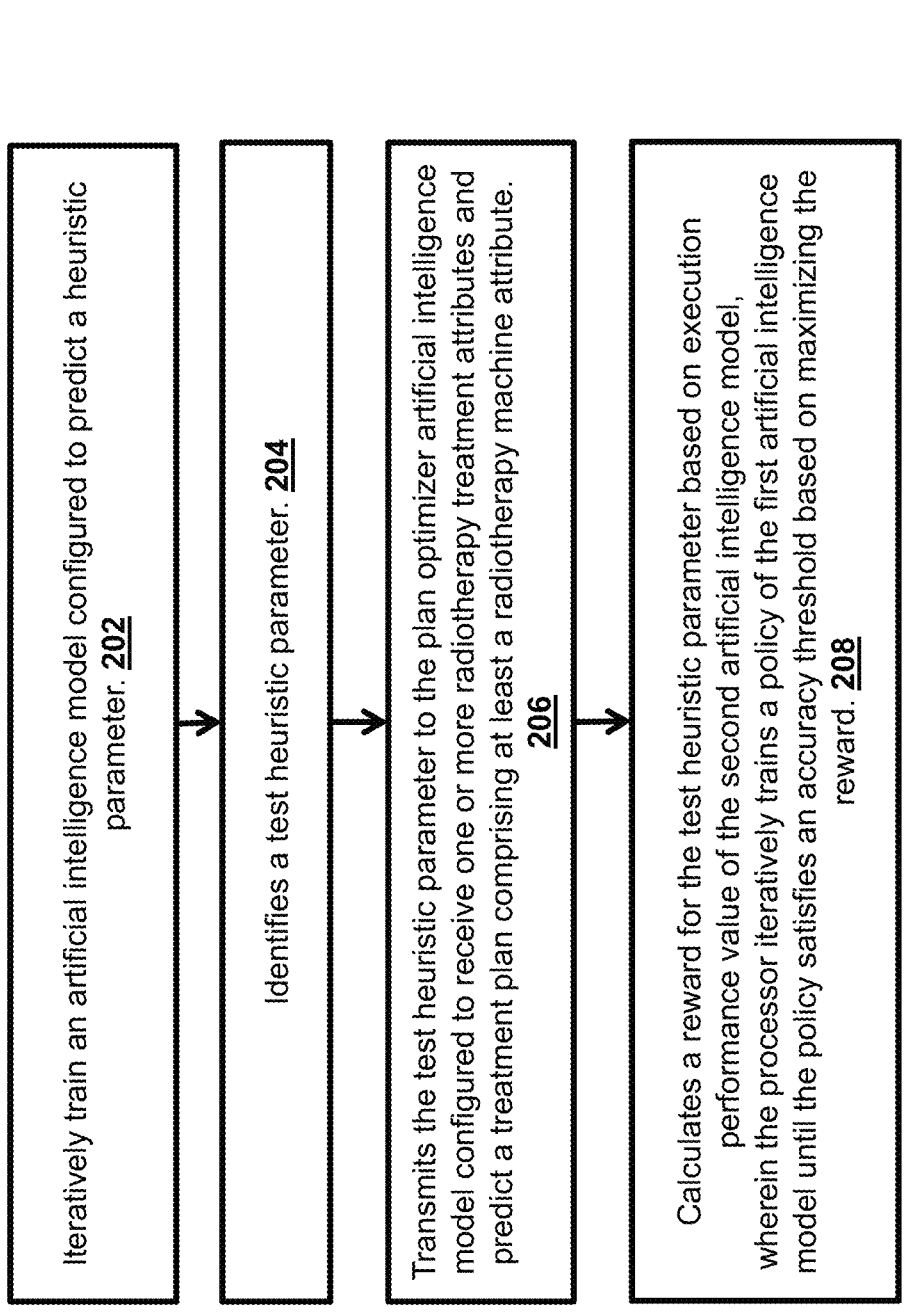

Iteratively train an artificial intelligence model configured to predict a heuristic parameter. 202

Identifies a test heuristic parameter. 204

Transmits the test heuristic parameter to the plan optimizer artificial intelligence model configured to receive one or more radiotherapy treatment attributes and predict a treatment plan comprising at least a radiotherapy machine attribute. 206

Calculates a reward for the test heuristic parameter based on execution performance value of the second artificial intelligence model, wherein the processor iteratively trains a policy of the first artificial intelligence model until the policy satisfies an accuracy threshold based on maximizing the reward. 208

Action $a_t$

Action $a_t$

Agent
302a

Environment
304a

Agent
302m

Environment
304m

State $s_t$

Reward $r_t$

State $s_t$

Reward $r_t$

Context

Context

Global Model
432

Policy
344

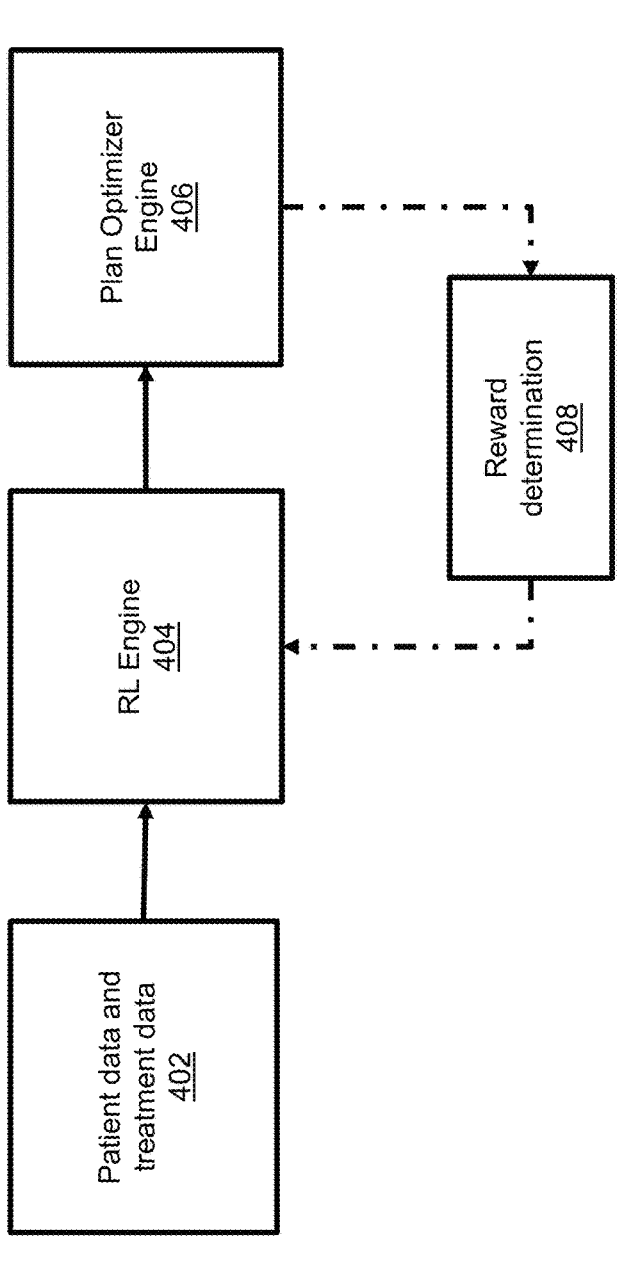
FIG. 4

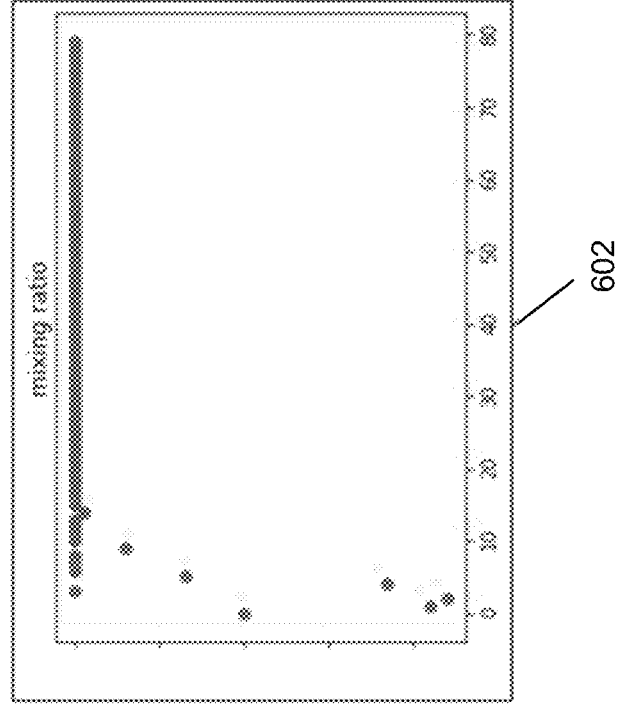
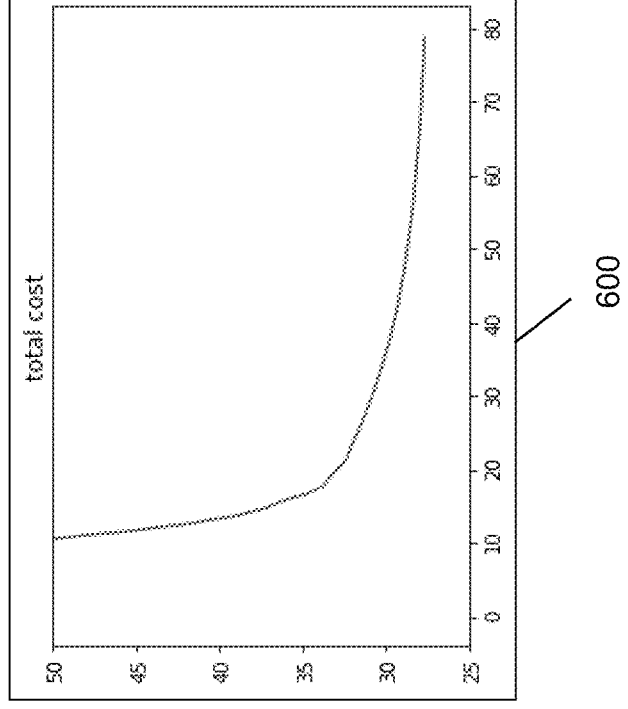
FIG. 6

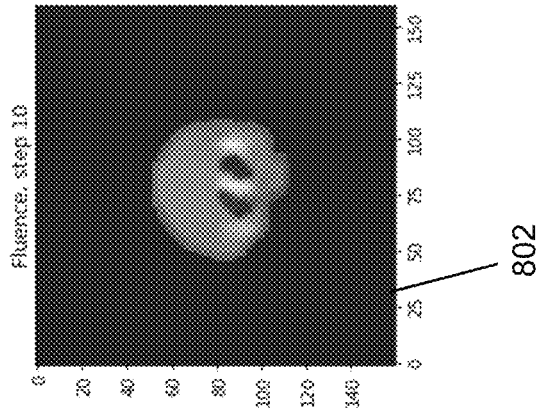
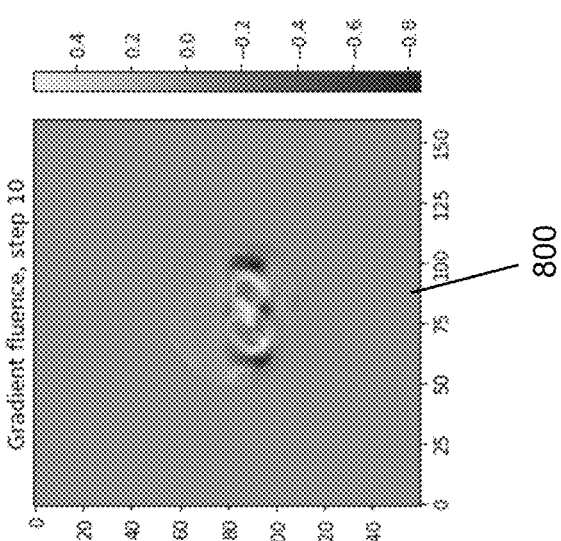
FIG. 8

MACHINE LEARNING MODELING TO PREDICT HEURISTIC PARAMETERS FOR RADIATION THERAPY TREATMENT PLANNING

TECHNICAL FIELD

This application relates generally to using machine learning modeling to suggest radiotherapy treatment attributes in radiation therapy treatment procedures.

BACKGROUND

Radiotherapy (radiation-based therapy) is used as a cancer treatment by emitting high doses of radiation that can kill cells or shrink a tumor. The target region of a patient's anatomy that is intended to receive radiation (e.g., tumor) is referred to as the planning target volume (PTV). Due to the extreme nature of the radiation emitted from the radiation therapy machine, it is imperative that a treatment plan is precisely calculated and followed. The goal of the treatment plan is to allow the radiotherapy machine to deliver enough radiation to the PTV to kill the cancerous cells. However, this goal must be balanced against the risk of damaging or harming other cells that belong to other organs or anatomical regions that are adjacent to, or surrounding, the PTV. These organs or anatomical regions are referred to as organs at risk (OARs).

A treatment plan may identify various attributes of a radiotherapy machine configured for the patient's treatment, such as intensity-modulated radiation therapy (IMRT) parameters (e.g., the number of radiation beams and the beam angles (radiation delivery directions)), volumetric modulated arc therapy (VMAT) parameters (e.g., number and extent of arcs (full or partial)), collimator angles, collimator jaw positions, avoidance sectors, isocenter positioning strategy, couch rotation, couch angles and the like.

Conventional methods of generating treatment plans involved a manual process in which a team of medical professionals would review a patient's attributes and diagnosis and generate a treatment plan accordingly. This process involves a time-consuming and tedious trial and error process that is inefficient and produces unreliable results. In order to improve this process, some approaches utilize machine learning models or other heuristic approaches to generate a treatment plan. These models are referred to herein as "plan optimizer models" or "plan optimizers." However, these computer-specific approaches have also faced technical challenges. For instance, various heuristic parameters used by these plan optimizer models must be inputted by the medial professionals, which creates inefficiencies and produces results that are dependent upon the medical professionals' subjective understanding and judgment. To improve this process, certain plan optimizer models impute the heuristic parameters themselves as part of generating a treatment plan. However, imputing the heuristic parameters is itself a time-consuming process that requires high computing resources.

SUMMARY

For the aforementioned reasons, there is a need to impute heuristic parameters used by computer models that generate treatment attributes, such that generating treatment plans can be performed using less computing resources and in a more timely manner. There is also a need to generate heuristic parameters that do not depend on subjective skills and understanding of medical professionals. Disclosed herein are systems and methods capable of offering continually refined parameters that can be ingested by a plan optimizer model to generate a treatment plan. Using the medical professional's prior decisions and previous treatments, a continuously trained machine learning model may be used to predict one or more parameters needed to efficiently run a plan optimizer model.

The machine learning model described herein may be trained using a reinforcement learning approach. The reinforcement learning approach utilizes agents and a dynamically changing (e.g., learning) policy to generate a parameter to be ingested by a plan optimizer model. Therefore, the model discussed herein can be trained without a predefined (e.g., labeled) training dataset, as required by other training techniques, such as supervised learning techniques.

The methods and systems described herein allow the machine learning model to gradually adapt to new data distributions (e.g., via an exploration phase), making the machine learning model less sensitive (more resistant) to data distribution changes. For example, in some implementations, a new solution(s) may be added. As a result, the machine learning model may be able to accommodate a new solution(s).

The reinforcement learning approach discussed herein can learn to predict parameters needed by a plan optimizer model to generate a treatment plan depending on patient data as context. Patient data may include medical images (computed tomography (CT) images, cone beam CT images (CBCT), four-dimensional CT images (e.g., CT images over time), magnetic resonance imaging (MRI) images, positron emission tomography (PET) images, ultrasound images, images obtained via some other imaging modality, or a combination thereof), patient information (e.g., height, weight, body mass index (BMI), diagnosis information (including anatomical attributes such as PTVs and/or OARs), age, equipment (e.g., pacemaker, respirator)), and the like.

The reinforcement learning approach described herein may learn to replicate (or simulate) the way in which a medical professional or a machine learning model would determine heuristic parameters. The machine learning model uses a reinforcement learning approach and is trained in response to cumulative reward information associated with a parameter generating the best and/or most efficient treatment plan when ingested by a plan optimizer model.

In one embodiment, a method of configuring a plan optimizer model for radiotherapy treatment comprises iteratively training, by a processor, a machine learning model configured to predict a heuristic parameter, wherein with each iteration, an agent of the machine learning model: identifies a test heuristic parameter; transmits the test heuristic parameter to the plan optimizer model configured to receive one or more radiotherapy treatment attributes and predict a treatment plan; and identifies a reward for the test heuristic parameter based on execution performance value of the plan optimizer model, wherein the processor iteratively trains a policy of the machine learning model until the policy satisfies an accuracy threshold based on maximizing the reward.

The category of the test heuristic parameter may correspond to at least one of a conjugate gradient mixing ratio, initial step length in line search, or a number of leaf tip mutation trials.

The reward may be based on whether the plan optimizer model converges upon a predicted treatment plan.

The reward may be based on an execution time of the plan optimizer model.

The heuristic parameter may correspond to the test heuristic parameter having a maximum reward.

The treatment plan may comprise at least one radiotherapy machine attribute.

At least one radiotherapy machine attribute may correspond to at least one of a couch angle, couch rotation attribute, or collimator angle settings.

The reward may be based on a number of iterations for the plan optimizer model.

The plan optimizer model may be a machine learning model.

The test heuristic parameter may be within a defined range of values.

In another embodiment, a server comprises a processor and a non-transitory computer-readable medium containing instructions for configuring a plan optimizer model for radiotherapy treatment that when executed by the processor, the instructions cause the processor to perform operations comprising iteratively training a machine learning model configured to predict a heuristic parameter, wherein with each iteration, an agent of the machine learning model identifies a test heuristic parameter; transmits the test heuristic parameter to the plan optimizer model configured to receive one or more radiotherapy treatment attributes and predict a treatment plan; and identifies a reward for the test heuristic parameter based on execution performance value of the plan optimizer model, wherein the processor iteratively trains a policy of the machine learning model until the policy satisfies an accuracy threshold based on maximizing the reward.

A category of the test heuristic parameter may correspond to at least one of a conjugate gradient mixing ratio, initial step length in line search, or a number of leaf tip mutation trials.

The reward may be based on whether the plan optimizer model converges upon a predicted treatment plan.

The reward may be based on an execution time of the plan optimizer model.

The heuristic parameter may correspond to the test heuristic parameter having a maximum reward.

The treatment plan may comprise at least one radiotherapy machine attribute.

The at least one radiotherapy machine attribute may correspond to at least one of a couch angle, couch rotation attribute, or collimator angle settings.

The reward may be based on a number of iterations for the plan optimizer model.

The plan optimizer model may be a machine learning model.

The test heuristic parameter may be within a defined range of values.

In yet another embodiment, a system for configuring a plan optimizer model for radiotherapy treatment, the system comprises the plan optimizer model configured to receive one or more radiotherapy treatment attributes and predict a treatment plan; and a server in communication with the plan optimizer, the server configured to: iteratively train a machine learning model configured to predict a heuristic parameter, wherein with each iteration, an agent of the machine learning model: identifies a test heuristic parameter; transmits the test heuristic parameter to the plan optimizer model; and identifies a reward for the test heuristic parameter based on execution performance value of the plan optimizer model, wherein the server iteratively trains a policy of the machine learning model until the policy satisfies an accuracy threshold based on maximizing the reward.

The category of the test heuristic parameter may correspond to at least one of a conjugate gradient (CG) mixing ratio, initial step length in line search, or a number of leaf tip mutation trials.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 2 illustrates a flow diagram of a radiotherapy treatment attribute recommendation system, according to an embodiment.

FIGS. 4-5 illustrate a workflow utilizing the methods and systems described herein, according to an embodiment.

FIG. 6 illustrates a cost function and mixing ratio values, according to an embodiment.

FIG. 8 illustrates a fluence map and a gradient fluence map, according to an embodiment.

DETAILED DESCRIPTION

Figure 1:
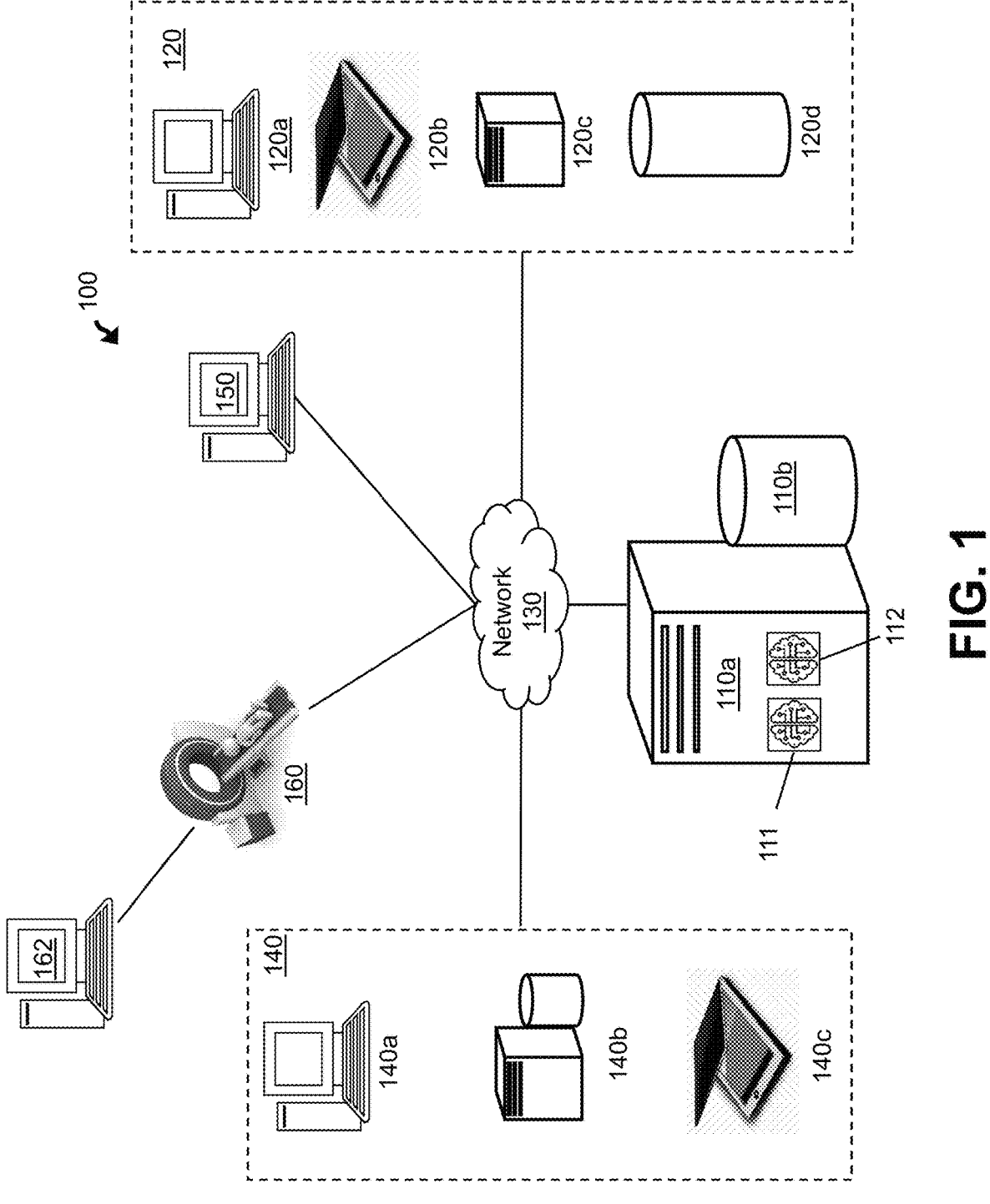
FIG. 1 illustrates components of a radiotherapy treatment attribute recommendation system, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

FIG. 1 illustrates components of a radiotherapy treatment attribute recommendation system 100, according to an embodiment. The system 100 may include an analytics server 110a, system database 110b, machine learning models 111-112, electronic data sources 120a-d (collectively electronic data sources 120), end-user devices 140a-c (collectively end-user devices 140), an administrator computing device 150, and a medical device 160 having a medical device computer 162. Various components depicted in FIG. 1 may belong to a radiotherapy clinic at which patients may receive radiotherapy treatment, in some cases via one or more radiotherapy machines located within the clinic (e.g., medical device 160).

The above-mentioned components may be connected to each other through a network 130. Examples of the network 130 may include, but are not limited to, private or public LAN, WLAN, MAN, WAN, and the Internet. The network 130 may include wired and/or wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), EDGE (Enhanced Data for Global Evolution) network.

The system 100 is not confined to the components described herein and may include additional or other components, not shown for brevity, which are to be considered within the scope of the embodiments described herein.

The analytics server 110a may train and execute the computer model 111 (including artificial intelligence and/or machine learning models) to recommend heuristic parameters for a secondary model (computer model 112). More specifically, the computer model 112 may be machine learning model that is configured to retrieve patient data and treatment data, such as patient's physical attributes, treatment characteristics (e.g., tumor location and other information received via a treating physician), and other relevant data from the data sources 120. The computer model 112 is then configured to analyze the data and display the data on an electronic platform accessed by the end-user devices 140, the administrator computing device 150, and/or the medical device computer 162. In some embodiments, the computer model 112 is a plan optimizer model.

The electronic platform may display one or more optimized (recommended, identified, selected) radiotherapy treatment attributes such as field geometry attributes determined from the machine learning model 111. The electronic platform may include graphical user interface (GUI) displayed on each electronic data source 120, the end-user devices 140, the administrator computing device 150, and/or the medical device computer 162. An example of the electronic platform generated and hosted by the analytics server 110a may be a web-based application or a website configured to be displayed on different electronic devices, such as mobile devices, tablets, personal computer, and the like.

In a non-limiting example, a medical professional may access the electronic platform using an end-user device 140 to input a patient's treatment characteristics and attributes. For instance, a treating physician may access the electronic platform to input the patient's physical attributes (e.g., height, weight or BMI) and diagnosis attributes (e.g., tumor location, medical images, PTV and/or OAR information, dose distribution thresholds) and any other information needed to perform the needed radiation therapy.

The analytics server 110a may execute the computer model 112 to generate a treatment plan and recommend radiotherapy treatment attributes used for proton radiation, photon radiation, and electron radiation for the patient. The treatment plan may include information such as a dose distribution, radiation parameters such as beam angles, side effect prediction, organ and/or tumor segmentation, machine therapy attributes such as couch angles, couch rotation attributes, gantry position, beam blocking devices, treatment frequency, treatment timing, and treatment modalities, among others. In order to allow the computer model 112 to execute more efficiently and/or in a more timely manner (faster), the analytics server may also execute the computer model 111 to generate one or more parameters that are used by the computer model 112. Before executing the computer model 111 in conjunction with the computer model 112, the analytics server may train the computer model 111 using training datasets collected from the electronic data sources 120, such as previous treatment plans and patient data.

Even though the computer model 112 is shown as being executed by the analytics server 110a, in other configurations, the computer model 112 may be stored in a third-party data repository and/or executed by a different server that may or may not be associated with the analytics server 110a. For instance, the analytics server 110a may transmit the predictions generated by the computer model 111 to a second server (a third-party server not shown in FIG. 1), such that the second server can execute a plan optimizer model and generate a treatment plan for the patient.

The analytics server 110a may be any computing device comprising a processor and non-transitory machine-readable storage capable of executing the various tasks and processes described herein. The analytics server 110a may employ various processors such as central processing units (CPU) and graphics processing unit (GPU), among others. Non-limiting examples of such computing devices may include workstation computers, laptop computers, server computers, and the like. While the system 100 includes a single analytics server 110a, the analytics server 110a may include any number of computing devices operating in a distributed computing environment, such as a cloud environment.

The analytics server 110a may execute software applications configured to display the electronic platform (e.g., host a website), which may generate and serve various webpages to each electronic data source 120 and/or end-user devices 140. Different users may use the website to view and/or interact with the recommended (optimized) results to select field geometry attributes for treatment. The analytics server 110a may be configured to require user authentication based upon a set of user authorization credentials (e.g., username, password, biometrics, cryptographic certificate, and the like). The analytics server 110a may access the system database 110b configured to store user credentials, which the analytics server 110a may be configured to reference in order to determine whether a set of entered credentials (purportedly authenticating the user) match an appropriate set of credentials that identify and authenticate the user.

The analytics server 110a may generate and host webpages based upon a particular user's role within the system 100. In such implementations, the user's role may be defined by data fields and input fields in user records stored in the system database of the clinic server 110b. The analytics server 110a may authenticate the user and may identify the user's role by executing an access directory protocol (e.g., LDAP). The analytics server 110a may generate webpage content that is customized according to the user's role defined by the user record in the system database 110b.

The analytics server 110a may use the methods described herein to train and/or execute the model 111, transmit the results to the computer model 112, and/or execute the computer model 112 to generate a treatment plan. The analytics server 110a may receive patient data (e.g., medical images, height, weight, diagnosis, age, equipment, etc.) from a user or retrieve such data from a data repository, analyze the data, and display the results on the electronic platform. The analytics server 110a may preprocess the patient data (e.g., automatically segment the medical image).

For instance, in a non-limiting example, the analytics server 110*a* may query and retrieve medical images from the database 120*d* and combine the medical images with segment data received from a medical professional operating the medical professional device 120*b* and/or medical device 160 to perform preprocessing on the medical image (e.g., segment the medical image).

The analytics server 110*a* may execute the methods discussed herein to display the results of execution of the computer model 111 and/or 112 via the electronic platform on the administrator computing device 150, the medical professional device 120*b*, medical device computer 162 and/or the end-user devices 140.

The electronic data sources 120 may represent various electronic data sources that contain, retrieve, and/or input data associated with a patient's treatment plan including patient data and treatment data. For instance, the analytics server 110*a* may use the clinic computer 120*a*, medical professional device 120*b*, server 120*c* (associated with a physician and/or clinic), and database 120*d* (associated with the physician and/or the clinic) to retrieve or receive data associated with the patient's treatment plan. The analytics server may use the data retrieved or received from the data sources 120 to train the computer model 111.

End-user devices 140 may be any computing device comprising a processor and a non-transitory machine-readable storage medium capable of performing the various tasks and processes described herein. Non-limiting examples of an end-user device 140 may be a workstation computer, laptop computer, tablet computer, and server computer. In operation, various users may use end-user devices 140 to access the GUI operationally managed by the analytics server 110*a*. Specifically, the end-user devices 140 may include clinic computer 140*a*, clinic server 140*b*, and a medical device professional 140*c*. Even though referred to herein as "end user" devices, these devices may not always be operated by end users. For instance, the clinic server 140*b* may not be directly used by an end user. However, the results stored onto the clinic server 140*b* may be used to populate various GUIs accessed by an end user via the medical professional device 140*c*.

The administrator computing device 150 may represent a computing device operated by a system administrator. The administrator computing device 150, along with the medical professional device 140*c*, medical professional device 120*b*, medical device computer 162, and the like, may be configured to display results from execution of the machine learning model 111 and/or the computer model 112. The administrator computing device 150 may also monitor the training of the machine learning model 111 and input various thresholds and training parameters, as needed. For instance, the administrator computing device 150 may review feedback and/or facilitate training or retraining (calibration) of the machine learning model 111 that are maintained by the analytics server 110*a*.

The medical device 160 may be a radiotherapy machine (e.g., a linear accelerator, particle accelerator (including circular accelerators), or a cobalt machine)) configured to implement a patient's radiotherapy treatment. The medical device 160 may also include an imaging device capable of emitting radiation such that the medical device 160 may perform imaging according to various methods to accurately image the internal structure of a patient. For instance, the medical device 160 may include a rotating system (e.g., a static or rotating multi-view system). A non-limiting example of a multi-view system may include a stereo systems (e.g., two systems may be arranged orthogonally).

The medical device 160 may also be in communication with a medical device computer 162 that is configured to display various GUIs discussed herein. For instance, the analytics server 110*a* may display the results predicted by the machine learning model 111 onto the medical device computer 162.

In operation, a medical professional may access an application executing on the medical professional device 120*b* and input patient data (e.g., patient information, patient diagnosis, radiation therapy radiation requirements and thresholds). The analytics server 110*a* then uses a patient identifier to query patient data (e.g., patient anatomy and/or medical images) from the electronic data sources 120. The analytics server 110*a* may then utilize the systems and methods described herein to generate recommended treatment plan to be displayed to (and interacted with) one or more medical professionals.

The analytics server 110*a* may be in communication (real-time or near real-time) with the medical device computer 162, end-user device 140 and/or electronic data sources 120, such that a server/computer hosting the medical device 160 can adjust the medical device 160 based on the recommended (or selected) treatment attributes within the treatment plan. For instance, the radiotherapy machine may adjust the gantry, beam blocking device (e.g., multi leaf collimator MLC), and couch based on field geometry attributes. The analytics server 110*a* may transmit instructions to the radiotherapy machines indicating any number or type of radiation parameters, beam angles, and/or treatment attributes to facilitate such adjustments.

In various embodiments, machine learning model 111 use one or more deep learning engines to simulate an agent in a reinforcement learning model. Although exemplified using deep convolutional neural networks, it should be understood that any alternative and/or additional deep learning model(s) may be used to implement deep learning engines. The deep learning engines include processing pathways that are trained continually and/or trained during training phase.

FIG. 2 illustrates a flow diagram of a radiotherapy treatment attribute recommendation system, according to an embodiment. While the systems and methods described herein relate to an initialization process executed prior to executing a radiotherapy treatment (and specifically, recommending parameters ingested by a plan optimizer model), it should be appreciated that the systems and methods described herein relate to other areas of radiation oncology and radiation therapy treatment planning where decisions are to be made from a set of pre-defined options. For instance, the method 200 may be executed to train a machine learning model, such that the trained model can be subsequently executed to monitor various parameters ingested by a plan optimizer model.

The method 200 may include steps 202-208. However, other embodiments may include additional or alternative steps, or may omit one or more steps altogether. The method 200 is described as being executed by a server, such as the analytics server described in FIG. 1. However, one or more steps of method 200 may be executed by any number of computing devices operating in the distributed computing system described in FIG. 1. For instance, one or more computing devices may locally perform part or all of the steps described in FIG. 2.

Efficient plan optimization may be an essential part of radiation therapy treatment. In some configurations, a plan optimizer model may be used as a part of interactive radiation therapy treatment planning or in on-couch adaptation. Plan optimizer models use various heuristic parameters to control the flow of optimization and to improve their performance. Non-limiting examples of these heuristic parameters may include IMRT conjugate gradient (CG) mixing ratio, initial step length in line search, rules guiding the advance to next multi-resolution level in VMAT, or number of leaf tip mutation trials done in one VMAT iteration.

Currently, these heuristic parameters are tuned and defined by engineers programming the plan optimizer models, such that they are mostly hard-coded within the optimization algorithm. For instance, plan optimizer models use either a set (e.g., predefined) heuristic parameter or an algorithm to identify the heuristic parameter used to perform various calculations that yield an optimized plan. The manual tuning of the heuristic parameters is a tedious process. Therefore, some plan optimizer models use a single set of heuristic parameters, regardless of the type of planning performed.

As an example, conventional methods usually mix a new gradient fluence with previous gradient fluences to use as the CG parameter for IMRT plan optimization. These methods then assign the mixing ratio to be the ratio of the L2 norms of the new and the old gradient fluences, following the Fletcher-Reeves (FR) method and/or other heuristic protocols. However, due to non-convexity of these values, the identified heuristic parameters may not be mathematically close to the value needed for the plan optimizer model to converge upon an optimized plan in an efficient (e.g., speedy) manner. In contrast, the method 200 provides a more systematic approach to identifying the heuristic parameters related to optimizer models.

Because it is difficult to deliver sufficient radiation dosage to PTV without irradiating nearby OARs, a patient's treatment may include dose-volume constraints (DVCs), which specify a given percentage of volume for each critical organ that can be sacrificed if necessary. The plan optimizer may iteratively change various attributes of the treatment (e.g., by changing speed and shape of the beam with a multi-leaf collimator (MLC)) and may iteratively predict how the change would result in radiation being applied to the patient's organs, clinical targets to be treated and body (or normal tissue). As used herein, fluence refers to a number of particles (such as photons or neutrons) applied to an area divided by a cross-section of the area itself. A fluence map is a representation of the fluence and visually depicts (e.g., using visual patterns or color mapping techniques) the number of particles per unit area with which the organ (or an area within the organ), clinical targets to be treated and body (or normal tissue) is irradiated.

Due to the inevitable hazardous radiation applied to OARs, radiation therapy for PTV will have an inherent cost to one or more OARs, which can be mathematically calculated. That is, when radiation is applied to the tumor, other parts of the patient will receive some radiation (cost). When optimizing treatment attributes of radiation therapy (e.g., IMRT), the goal is to minimize the cost function by adjusting treatment attributes using various heuristic parameters (e.g., adjusting fluence maps based on gradient fluence). The cost function itself can be mathematically defined in various ways based on the clinical goals of the planning. Referring to FIG. 6, the graph 600 represents the value of a cost function as a function of the iteration step of the optimizer. As depicted, the plan optimizer model iteratively adjusts (e.g., using non-linear methods) one or more attributes of the patient's treatment plan to gradually reduce the cost value.

In CG methods used in IMRT optimization, the gradient fluence is generally a weighted sum of current and previous gradient fluences (at step t and at step t−1), with a certain mixing ratio. The mixing ratio may be one of the heuristic parameters that has to be gradually adjusted. The mixing ratio (also known as the Fletcher-Reeves ratio) may be calculated from norms of gradient fluences, for instance using the following formula:

$$\text{Fletcher-Reeves mixing ratio} = \frac{(L_2 \text{ norm of fluence gradient at step } t)^2}{(L_2 \text{ norm of fluence gradient at step } t-1)^2}$$

Figure 7:
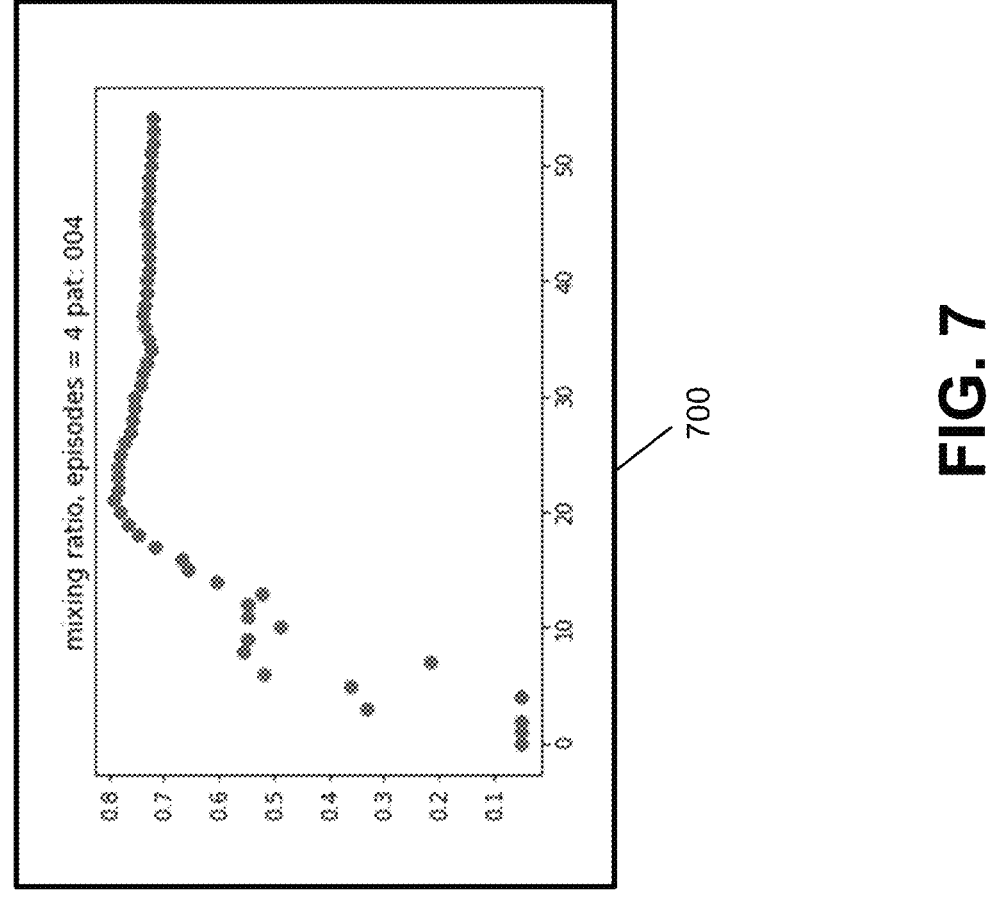
FIG. 7 illustrates mixing ratio values, according to an embodiment.

The goal of the plan optimizer model may be to identify a mixing ratio that would yield good results (e.g., reduces cost) when used to generate a treatment plan for a patient. In some embodiments, a ratio threshold may be imposed by the plan optimizer (or by a medical professional or a system administrator). For instance, as depicted in a graph 602, the mixing ratio is adjusted as the plan optimizer iterates and eventually plateaus. However, this value is not necessarily permitted to rise above a certain threshold (e.g., 0.6). Using the method 200, the mixing ratio can be independently calculated via an independently trained model, as depicted in FIG. 7. The predicted heuristic parameter can then be ingested by the plan optimizer model to generate a treatment plan for the patient.

Referring back to FIG. 2, in step 202, the analytics server may iteratively train a machine learning model configured to predict a heuristic parameter, wherein with each iteration, an agent of the machine learning model performs the steps 204-208 (at least partially).

Using the method 200, the analytics server may iteratively train a machine learning model using a reinforcement learning technique. Specifically, using a reinforcement learning technique, an agent of the machine learning model learns policies for choosing optimal settings for control/heuristic parameter values ingested by a second model (e.g., plan optimizer model). The training may occur in iterative steps where with each step, the agent may either explore or exploit knowledge to learn how to select a parameter that yields higher (or the most) rewards (e.g., maximum reward).

In the non-limiting example of CG method used for IMRT, the agent may iteratively train itself where (when trained) the agent can identify an optimal mixing ratio for the conjugate gradient method for updating gradient fluences. As used herein, optimal may refer to an action that would produce maximum rewards. Even though certain aspects of the present disclosure are described in terms of identifying CG for IMRT, it is understood that the methods and systems described herein apply to all parameters used by a computer model (whether machine learning or using other algorithms), such as the plan optimizer model, to generate and/or optimize a treatment plan.

Training the machine learning model using reinforcement learning techniques may provide better results than using supervised learning for optimization because reinforcement learning techniques can avoid compounding errors that can occur in supervised learning methods. Moreover, using a deep neural network based reinforcement learning policy for determining the heuristic parameters (e.g., mixing ratio) at any given time may also be better than using a static (heuristic) formula because the former can adapt to peculiar attributes and values.

Using method 200, the policy may respond the different features (or attributes and values) in the beginning of the optimization than at the end of optimization. For example, in the beginning of the optimization, the policy may have learned that only rough (or coarse-grained) overall features of the observation (such as total variation of the fluence gradient) are important to determine the heuristic parameter. In contrast, at end of the optimization, the policy may learn that the fine-grained features of the observation (such as changes in nearby pixels of the fluence gradient) are important for determining the heuristic parameter.

In step 204, the analytics server may identify a test heuristic parameter. With each iteration, the analytics server may use various reinforcement learning techniques to generate a test heuristic parameter. For instance, the analytics server may select a heuristic parameter from a set of possible heuristic parameters. The selection may depend upon whether the analytics server is in exploration or exploitation phase.

The analytics server may define data associated with a single patient data or a set of patients for the plan optimizer model. The plan optimizer model is then initialized. In some configurations, the analytics server may execute a few (e.g., defined number) initial iterations using the defined set of data. For instance, the analytics server or another processor associated with the plan optimizer model (e.g., third-party processor) may initialize the plan optimizer model using the optimizer's default settings. Using this protocol, the analytics server ensures that the plan optimizer model is assimilated for reinforcement learning.

In step 206, the analytics server may transmit the test heuristic parameter to the plan optimizer machine learning model configured to receive one or more radiotherapy treatment attributes and predict a treatment plan comprising at least a radiotherapy machine attribute. At step 208, the analytic server may identify (e.g., calculate or collect) a reward for the test heuristic parameter based on execution performance value of the second machine learning model, wherein the processor iteratively trains a policy of the first machine learning model until the policy satisfies an accuracy threshold based on maximizing the reward.

The agent may interface with the plan optimizer model (e.g., transmits data to the optimizer) using various techniques. The agent may transmit the test heuristic parameter generated in step 204 to the plan optimizer model. The analytics server may then execute the plan optimizer model using the test heuristic parameter generated in step 204 and monitor its performance. The analytics server may then tune and calibrate the agent (e.g. choice of the agent's hyperparameters) using various reinforcement learning techniques, such as proximal policy optimization technique, deep Q learning technique, asynchronous learning techniques, trust region policy optimization technique, and/or C51 technique.

With each iteration, a set of observable data (agent's observation from the environment) is transmitted to the agent. As used herein, observable data may include data associated with the performance of the plan optimizer model. Non-limiting examples of observable data may include data associated with fluences, gradient fluences, values of the cost function, and the like. The observation can also include, for example, observable data from the current and the previous iterations (e.g., whether a subsequent iteration is moving toward convergence). In some configurations, because the observable data may be received in form of an image (e.g. fluence map 800 or gradient fluence map 802 depicted in FIG. 8), the agent may utilize a feature extractor to analyze the received data (e.g., the feature extractor of the agent could be a convolutional neural network itself).

The analytics server may define an end state for the monitoring in various ways. The end state may identify that the plan optimizer model has reached a threshold and the agent may now identify (e.g., calculate or collect) a reward based on its observation. In one example, the end state may be defined as an indication where the plan optimizer model returns a specific status, such as "converged" a pre-defined convergence criterion, or another diagnostic value, or a preset number of trials. For instance, the analytics server may monitor a time that the plan optimizer model takes to converge upon a prediction, monitors how many iterations the plan optimizer model executes before converging upon a prediction, or monitors any other diagnostic value associated with the plan optimizer model.

The analytics server may define the action space for the agent as either a continuous or quasi-continuous variable that obtains values in relevant ranges. For instance, when training to predict CG for IMRT, the analytics server may define a range of [0-1] where the value corresponds to the mixing ratio. As discussed herein, during the training phase, the agent generates different test parameters and transmits them to the plan optimizer model and generates a reward for each test parameter accordingly. The range may be defined by a system administrator or defined automatically based on previous data analyzed. For instance, if similar cases yield parameters that are typically between [0-1], then the agent may not transmit test heuristic parameters to the plan optimizer model outside the range of [0-1]. As a result, when in production or prediction phase, the agent may also predict parameters within the same range (or even a smaller range).

The analytics server may use various methods to identify the reward associated with each heuristic parameter. For instance, the analytics server may define the reward in ways to optimally promote the agent's learning. In a non-limiting example, the reward may be a function of the number of iterations performed by the plan optimizer model to converge upon a prediction (e.g., plan). Using this reward system, the analytics server may select a reinforcement learning algorithm (e.g., as a deep Q learning or proximal policy) to train the agent.

After the training is completed in accordance with an accuracy threshold or any other defined thresholds, the policy of the machine learning model is trained and ready for the prediction phase. The trained policy may be represented, for example, as a neural network architecture with weights and biases. After training, the analytics server may store the policy (e.g., the architecture and code representing the weights and biases) as a data object within a data repository (e.g., computer memory or a shared data repository). When prompted, the analytics server can access the data object and execute the policy to allow the machine learning model to predict results for a new patient.

When trained, the machine learning model may predict a heuristic value that can be ingested by a plan optimizer model. For instance, chart 700 in FIG. 7, depicts an example of the machine learning model (having a trained policy) converging upon a mixing ratio. The trained policy may be implemented to be used in conjunction with the plan optimizer model or as a part of (implemented within the code for) the plan optimizer model. For example, the policy (e.g., biases and weights) can be included in the compiled code of the plan optimizer model as an embedded function.

Figure 3:
FIG. 3 illustrates a reinforcement learning model, according to an embodiment.

FIG. 3 illustrates a reinforcement learning model 300, according to an embodiment. The reinforcement learning model 300 is an example of how a server trains a policy of a machine learning model. The reinforcement learning model 300 depicts a multitude of certain features. However, in some implementations, a reinforcement learning model may only utilize a single feature. For instance, even though multiple agents are depicted in FIG. 3, some embodiments may only include one agent.

The model 300 is implemented to recommend radiotherapy treatment attributes of various radiotherapy treatment categories based a maximizing (or increasing) the cumulative sum of rewards. The context of the framework may be based on the previous treatment plans. The available actions in the solution space may be different parameters. The reward may be based on whether the recommended parameter produced efficient or acceptable results. For instance, a parameter that is ingested by a plan optimizer model and allows the plan optimizer model to generate results faster is assigned a higher rewards.

In the reinforcement learning model 300, an agent 302$a$-302$m$ (collectively referred to herein as agents 302) interacts with an environment 304 (e.g., environment 304$a$-304$m$ respectively). The environment 304 may refer to data associated with execution of the plan optimizer model using a test heuristic parameter. The agents 302 refer to the learner or trainer (e.g., the analytics server training the AI model or the AI model itself). With each recommendation task t, the agent 302 observes a state $s_t$ based on a context and selects an action from a set of actions using a policy 344. The analytics server may train the neural network using reinforcement learning because each state $s_t$ may be independent from the next state $s_{t+1}$.

The agent 302 may ingest data received by the model 300. In some implementations, the analytics server transforms and/or pre-processes the data. For example, the dimensionality of the data may be reduced before the agents 302 receive the data. The goal of the agent 302 may be to continuously learn and refine policy 344 and to recommend acceptable parameters that can be ingested by a plan optimizer model. The learning occurs as the agent 302 maximizes its cumulative reward. For instance, the agent 302 may receive a positive reward when the plan optimizer generates a plan that is accepted by a medical professional or generates a plan in a timely manner or fewer iterations.

The policy 344 may map states (and observations) to actions. The policy 344 may provide the probability of taking a certain action when the agent 302 is in a certain state. The possible set of actions may include different heuristic parameters. The possible set of actions (e.g., action space) may be arbitrarily defined and depend on the solution space considerations. For example, the solution space may be different depending different patient attributes and/or different treatment attributes.

The agents 302 may select an action based on the value of taking each action, where the value of selecting the action is defined as the expected reward received when taking that action from the possible set of actions. The agents 302 may select actions based on exploratory actions and exploitation actions. The agent may be continuously or periodically optimizing its current and future performances as it balances exploitation and exploration and aims to generalize to new contexts.

An exploratory action improves an agent's knowledge about an action by using the explored action in a sequence resulting in a reward identification/collection. An exploratory action is an action unrestricted by prior knowledge. An exploitation action is a "greedy" action that exploits the agent's 302 current action-value estimates. For example, when the epsilon indicates the exploration action, the policy 344 may direct the agent 302 to select a random action. In contrast, when the epsilon indicates the exploitation action, the policy 344 may direct the agent 302 to select an action that has previously received a reward given one or more similar patient data characteristics.

In some embodiments, the analytics server may inject parameter noise into the model 300. Parameter noise may result in greater exploration and more successful model 300 by adding noise to the parameters of the policy selection. Using epsilon-greedy action selection, for example, the agent 302 balances exploratory actions and exploitation actions. The agent 302 may select an epsilon value and perform an exploitation action or an exploratory action based on the value of the epsilon and one or more exploitation and/or exploration thresholds. The agent 302 may randomly select an epsilon value, select an epsilon value from a predetermined distribution of epsilon values, select an epsilon value in response to the environment 304, select an epsilon value in response to one or more criteria, select an epsilon value in response to the number of training epochs, select an epsilon value in response to one or more gradients, and the like.

In some embodiments, as training progresses, exploitation actions may be leveraged to refine training the experts. For example, the analytics server may revise the epsilon value (or epsilon selection method) such that the likelihood of the exploration action is higher or lower than the likelihood of the exploitation action. Additionally, or alternatively, the analytics server may revise the exploitation action threshold and/or the exploration action threshold.

Agents 302 may also select an action using policy 344. The policy 344 may be a global policy such that the agents 302 share a common policy. The policy 344 may be tuned based on the value of taking each action, where the value of selecting the action is defined as the expected reward received when taking that action from the possible set of actions. In some configurations, the analytics server may update the policy 344 using agents operating in other servers (e.g., via federated learning).

The policy 344 may be stored in a global model 332. Using the global model 332 allows each agent 302 to have a more diversified training dataset and eliminates a need for synchronization of models associated with each agent 302. The global model 332 with agents 302$a$ to 302$m$ may produce an m-dimensional output. In other configurations, there may be models associated with each agent (e.g., m models), and each agent may identify/collect a reward using a designated machine learning model. Each agent may tune its own policy. The policy class of the agent may be represented by a general linear classifier, support vector machine, random forest, or another machine learning model (e.g., deep neural network).

In response to selecting an action (or multiple actions), the agent 302 may receive feedback, indicating how the action affected the environment 304. In some configurations, the agent 302 evaluates the feedback. The feedback may be received from the plan optimizer model. In another embodiment, the analytics server (or any other processor) may monitor performance of the plan optimizer and may generate the reward accordingly.

With each iteration (or after multiple iterations and/or steps), the agent 302 selects a policy 344 (and an action) based on the current state $s_t$, the epsilon value, and the agent 302 (or the machine learning model) identifies/collects a reward. Each iteration, the agent 302 (or machine learning model) learns to perform better as can be seen in the increase of the rewards (e.g., an iterative summation of rewards).

Figure 5:
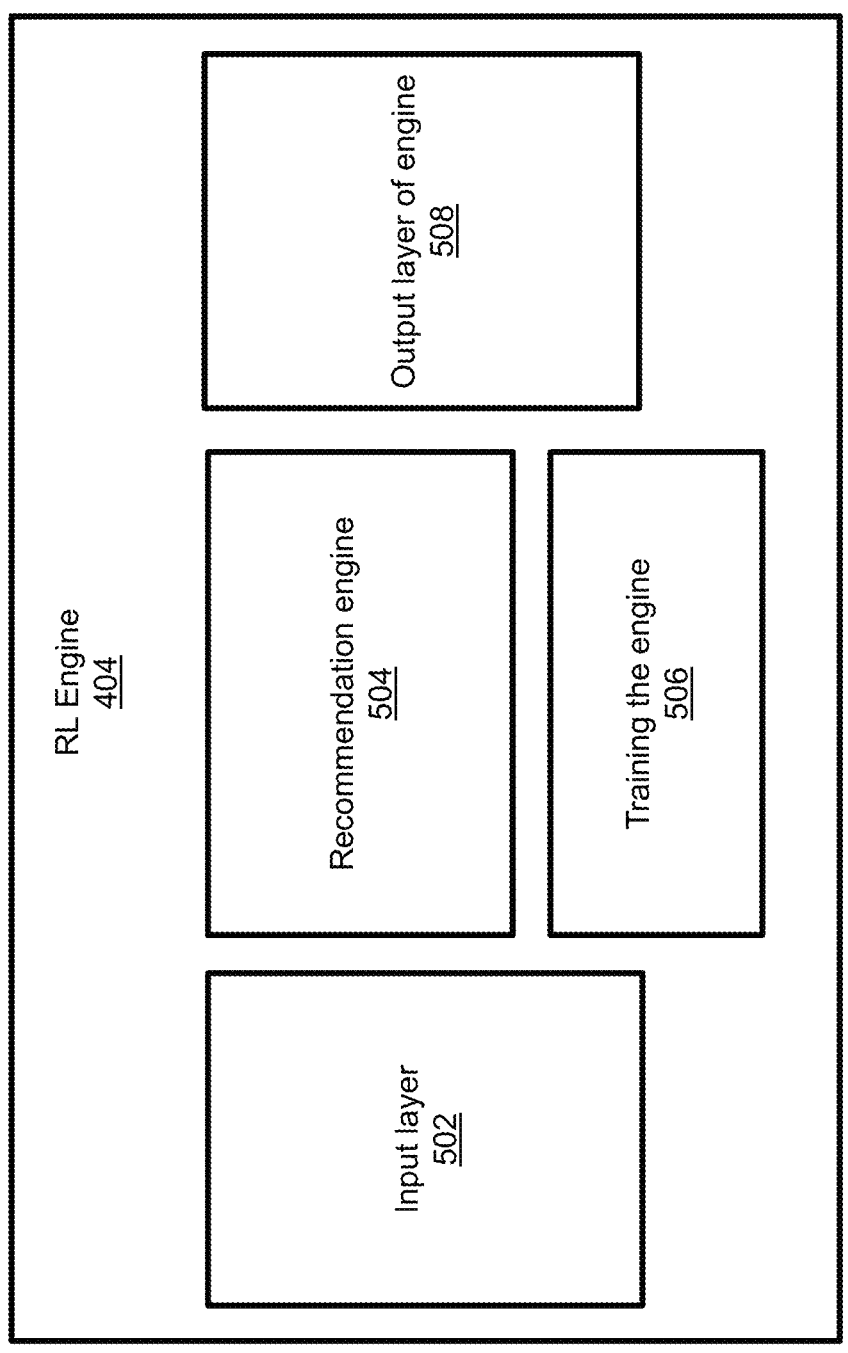

FIGS. 4-5 illustrate a non-limiting visual example of a workflow 400 utilizing the methods and systems described herein, according to an embodiment. In this example, the analytics server receives and analyzes patient data and/or treatment attributes to predict an optimized heuristic parameter used by a plan optimizer model (e.g., the plan optimizer engine 406). The analytics server may first receive patient data and treatment data 402 for a particular patient. The data 402 may include medical images and/or patient information in addition to treatment data (e.g., tumor identified or other recommendations inputted by a treating physician). The data 402 may be ingested by reinforcement learning (RL) engine 404. FIG. 5 illustrates a RL engine 404 employed in the workflow 400, according to an embodiment.

The input layer 502 may be used to ingest data that may or may not be heterogeneous. In some implementations, the input layer 502 may reduce the dimensionality of the data received. For example, the input layer 502 may be implemented using a convolutional layer and/or a pooling layer. The convolutional layer may receive the data (or a pre-processed version of the patient data and/or treatment data). For example, pre-processing the data may include the analytics server executing feature extracting protocols, normalizing the data, scaling the data, flattening the data, transforming the data into a different dimension, and the like.

A convolutional layer in the input layer 502 may detect and extract features of the data (e.g., data 402 in FIG. 4) by convolving a filter and/or kernel with the patient data and generating a feature map of the extracted features. Convolving the patient data with the filter has the effect of reducing the dimensions of the patient data. The output of the convolutional layer may be a feature map. In some embodiments, there may be one or more convolutional layers after the convolutional layer. Increasing the number of convolutional layers increases the complexity of the features detected in the feature map. If additional convolutional layers are employed, the filters in the subsequent convolutional layers may be the same as the filters employed in the first convolutional layer. Additionally, or alternatively, the filters used in the subsequent convolutional layers may be different from the filters employed in the first convolutional layer.

The feature map may be fed into a pooling layer. The pooling layer may be a max pooling layer (or any other type of pooling later) that detects prominent features. In other configurations, the pooling layer may be an average pooling layer. The pooling layer reduces the dimensionality of the feature map to down sample the feature map for more efficient operation. In an example, if the pooling layer is a max pooling layer, then the analytics server detects the prominent features having higher relative values in a pooling window.

The recommendation engine 504 may be a machine learning model (e.g., a neural network) or a generalized linear model based on input features determined from the input layer 502. The recommendation engine 504 may be a global engine (e.g., global model 332 in FIG. 3) or include separate sub-engines for each radiotherapy attribute (and/or category of radiotherapy treatment). Accordingly, there may be n models indicating n field geometry attribute options.

The output layer 508 may convert an output from the recommendation engine 504 into a recommendation score (or other probability associated with a medical profession-al's predicted field geometry or other attribute preference). In the event the recommendation engine 504 is a neural network, for instance, the output layer 508 may be a softmax layer. The softmax layer may use a softmax function, or a normalized exponential function, to transform an input of real numbers (e.g., the output of the recommendation engine

504) into a normalized probability distribution over predicted output classes (e.g., radiotherapy treatment attributes and/or categories of radiotherapy treatment). In the event the recommendation engine 504 is a linear model, the output layer 508 may be a list of recommendations with an assigned probability.

The recommendation engine 504 may be trained using the methods and systems discussed herein. For instance, the reward determination 408 calculates a reward for different possible actions and the analytics server may train the recommendation engine 504 accordingly. Specifically, the parameters predicted by the recommendation engine 504 may be ingested by the plan optimizer engine 406. The analytics server may then observe the treatment generated by the plan optimizer engine 406. For instance, the analytics server may determine a time associated with the execution of the plan optimizer engine 406 when generating a treatment plan based on a predicted parameter. For instance, based on the time it takes the plan optimizer engine 406 to generate the plan, the analytics server may generate a score (reward) for the parameter recommended by the recommendation engine 504. Using reinforcement learning methods and systems described herein, the analytics server may train the recommendation engine 504.

The output layer 508 may output the results to a computing device (e.g., display the results for a medical professional and/or a system administrator). For example, the output layer 508 may select the top n recommendations for display. In a different example, the output layer 508 may rank the recommendations from most recommended to least recommended.

After the completion of the training phase (e.g., a threshold number of training iterations or a threshold recommendation accuracy), the recommendation engine 504 is ready to predict parameters (prediction phase). Accordingly, the training phase is clearly distinguished from a prediction phase using dashed lines. During the prediction phase, the 504 may generate a heuristic parameter and transmit the heuristic parameter to the plan optimizer engine 406 where the plan optimization engine generates a treatment plan for the patient.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method of configuring a plan optimizer model for radiotherapy treatment using a machine learning model, the method comprising:

iteratively training, by a processor, the machine learning model implemented as a reinforcement learning agent configured to predict a heuristic parameter corresponding to a conjugate gradient mixing ratio, wherein with each iteration, an agent of the machine learning model:

identifies a test heuristic parameter;

transmits the test heuristic parameter to the plan optimizer model configured to receive one or more radiotherapy treatment attributes and predict a treatment plan generated based on the conjugate gradient mixing ratio; and identifies a reward for the test heuristic parameter based on execution performance value of the plan optimizer model, the execution performance value comprising at least one measure of treatment plan quality and at least one indicator of operational performance of the plan optimizer model, wherein the processor iteratively trains a policy of the machine learning model until the policy satisfies an accuracy threshold based on maximizing the reward; and configuring, by the processor, the plan optimizer model based on a predicted test heuristic parameter predicted by the machine learning model.

2. The method of claim 1, wherein a category of the test heuristic parameter further corresponds to an initial step length in line search or a number of leaf tip mutation trials.

3. The method of claim 1, wherein the reward is based on whether the plan optimizer model converges upon a predicted treatment plan.

4. The method of claim 1, wherein the reward is based on an execution time of the plan optimizer model.

5. The method of claim 1, wherein the heuristic parameter corresponds to the test heuristic parameter having a maximum reward.

6. The method of claim 1, wherein the treatment plan comprises at least one radiotherapy machine attribute.

7. The method of claim 1, wherein the reward is based on a number of iterations for the plan optimizer model.

8. The method of claim 1, wherein the plan optimizer model is a machine learning model.

9. The method of claim 1, wherein the test heuristic parameter is within a defined range of values.

10. A server comprising a processor and a non-transitory computer-readable medium containing instructions for configuring a plan optimizer model for radiotherapy treatment using a machine learning model, that when the instructions are executed by the processor, the instructions cause the processor to perform operations comprising:

iteratively training the machine learning model implemented as a reinforcement learning agent configured to predict a heuristic parameter, wherein with each iteration, an agent of the machine learning model:

identifies a test heuristic parameter;

transmits the test heuristic parameter to the plan optimizer model configured to receive one or more radiotherapy treatment attributes and predict a treatment plan generated based on a conjugate gradient mixing ratio;

identifies a reward for the test heuristic parameter based on execution performance value of the plan optimizer model, the execution performance value comprising at least one measure of treatment plan quality and at least one indicator of operational performance of the plan optimizer model, wherein the processor iteratively trains a policy of the machine learning model until the policy satisfies an accuracy threshold based on maximizing the reward; and

configures the plan optimizer model based on a predicted test heuristic parameter predicted by the machine learning model.

11. The server of claim 10, wherein a category of the test heuristic parameter further corresponds to an initial step length in line search or a number of leaf tip mutation trials.

12. The server of claim 10, wherein the reward is based on whether the plan optimizer model converges upon a predicted treatment plan.

13. The server of claim 10, wherein the reward is based on an execution time of the plan optimizer model.

14. The server of claim 10, wherein the heuristic parameter corresponds to the test heuristic parameter having a maximum reward.

15. The server of claim 10, wherein the treatment plan comprises at least one radiotherapy machine attribute.

16. The server of claim 10, wherein the reward is based on a number of iterations for the plan optimizer model.

17. The server of claim 10, wherein the plan optimizer model is a machine learning model.

18. The server of claim 10, wherein the test heuristic parameter is within a defined range of values.

19. A system for configuring a plan optimizer model for radiotherapy treatment using a machine learning model, the system comprising:

the plan optimizer model configured to receive one or more radiotherapy treatment attributes and predict a treatment plan; and a server in communication with the plan optimizer model, the server comprising a processor and a non-transitory computer readable medium containing instructions that, when executed by the processor, cause the processor to:

iteratively train the machine learning model implemented as a reinforcement learning agent configured to predict a heuristic parameter corresponding to a conjugate gradient mixing ratio, wherein with each iteration, an agent of the machine learning model:

identifies a test heuristic parameter;

transmits the test heuristic parameter to the plan optimizer model; and identifies a reward for the test heuristic parameter based on execution performance value of the plan optimizer model, the execution performance value comprising at least one measure of treatment plan quality and at least one indicator of operational performance of the plan optimizer model, wherein the server iteratively trains a policy of the machine learning model until the policy satisfies an accuracy threshold based on maximizing the reward; and configure the plan optimizer model based on a predicted test heuristic parameter predicted by the machine learning model.

20. The system of claim 19, wherein a category of the test heuristic parameter further corresponds to an initial step length in line search or a number of leaf tip mutation trials.

* * * * *